United States Patent [19]

Eberle

[11] Patent Number: 4,612,873
[45] Date of Patent: Sep. 23, 1986

[54] CENTRIFUGE CHAMBER FOR CYTODIAGNOSTIC INVESTIGATION OF EPITHELIAL CELLS CONTAINED IN A SAMPLE

[75] Inventor: Günter Eberle, Tuttlingen, Fed. Rep. of Germany

[73] Assignee: Firma Andreas Hettich, Tuttlingen, Fed. Rep. of Germany

[21] Appl. No.: 529,126

[22] Filed: Sep. 2, 1983

[30] Foreign Application Priority Data

Sep. 2, 1982 [DE]  Fed. Rep. of Germany ....... 3232581

[51] Int. Cl.[4] .................... G01N 33/48; G01N 1/28; B05C 11/08
[52] U.S. Cl. .................................. 118/52; 118/411; 422/72; 435/310; 436/45; 436/63; 494/17
[58] Field of Search ................... 118/52, 411; 422/72, 422/102; 435/292, 294, 310, 312, 317; 436/63, 45, 46; 494/16–18, 85; 424/3

[56] References Cited

U.S. PATENT DOCUMENTS

| | | | |
|---|---|---|---|
| 3,977,598 | 8/1976 | McDonald | 422/72 X |
| 3,994,594 | 11/1976 | Sandrock et al. | 422/102 X |
| 4,192,250 | 3/1980 | van Duijn | 118/52 |
| 4,241,005 | 12/1980 | Rothschild et al. | 118/52 X |
| 4,250,830 | 2/1981 | Leif | 118/52 |
| 4,423,699 | 1/1984 | Boeckel et al. | 118/52 |

OTHER PUBLICATIONS

Watson; A Slide Centrifuge: An Apparatus for Concentrating Cells in Suspension on a Microscope Slide; J. Lab. & Clin. Med., vol. 68, No. 3, 494–501, 9/'66.

Primary Examiner—Barry S. Richman
Assistant Examiner—Michael S. Gzybowski
Attorney, Agent, or Firm—Antonelli, Terry & Wands

[57] ABSTRACT

A centrifuge chamber for cytodiagnostic investigation of epithelial cells contained in a sample, wherein a cell suspension investigated is placed in a first bore of a sample chamber containing a plurality of bores disposed parallel to one another and subjected to a centrifuging process. During a centrifuging process, the sample fluid is separated into a proximal fraction and a distal fraction, and the proximal fraction is then separated by the centrifuging process so that it is transferred via a flow connection provided between the first and second bores, into the second bore. In addition to automatic separation of the proximal and distal fractions during the centrifuging process, it is also possible to perform a staining procedure during the centrifuging process. The result of the process is a slide, having at least two different slide fields, whereby the slide field associated with the first bore is coated with the epithelial cells to be investigated and then stained, while the slide field associated with the second bore is stained as a control field, likewise during the centrifuging process.

9 Claims, 25 Drawing Figures

CENTRIFUGE CHAMBER FOR CYTODIAGNOSTIC INVESTIGATION OF EPITHELIAL CELLS CONTAINED IN A SAMPLE

The invention relates to a method of cytodiagnostic investigation of epithelial cells contained in a sample, and centrifugal chamber for carrying out the method steps (a) to (i).

In a method for cytodiagnostic investigation of epithelial cells contained in a test sample, a suspension sample containing cells to be investigated is sedimented by a first centrifuging process, with the resulting cell sediment being drawn off. The cell sediment drawn off is smeared on a separating medium such as, for example, plasmasteril. The sample suspension is subjected to a second centrifuging process to form a distal and proximal fraction which are then separated and each placed in a bore of a centrifugal chamber and then subjected to a third centrifuging process whereby a slide, disposed in the centrifugal chamber, is coated with the epithelial cells and the cells sedimented on the slide are stained and optically examined.

The method involves isolating epithelial cells obtained in a smear and depositing them side by side as uniformly as possible on a slide. Dirt as well as numerous nuclei, erythrocytes, leukocytes, etc. are largely separated by fractionation and pipetted off as supernatant (light fraction). Both fractions, the distal and the proximal (supernatant), are then centrifuged separately, each onto a slide, with one slide serving for identification, evaluation, and counting of the epithelial cells and the other slide serving to determine that unimportant parts of the desired epithelial cells are still present in the supernatant, and that the first slide constitutes a representative image of the smear.

The previous method is described in the journal *Biotechnische Umschau*, No. 4, 1978 under the title "Ein Verfahren zur isolierten Deposition von Zellen der Cervix uteri auf Glasobjekttraeger" (A Method for Isolated Deposition of Cells from the Cervix Uteri on Glass Slides) and in the journal *Tumor Diagnostik*, No. 2, pp. 35–38, 1981, and in the *Journal of Histochemistry and Cytochemistry*, Vol. 27, pp. 14–18, 1979 as well as in the journal *Acta histochemica*, Suppl. Vol. XXI, pp. 137–145, 1980.

In the known methods, a total of three centrifugations are required. In the first step, after shaking the suspension samples with a cotton carrier, whereby the cotton carrier contains the cells to be investigated, the cotton carrier and coarse impurities are removed by pouring the suspension through a nylon screen. The suspension samples are then sedimented in a second work step using a centrifuge for ten minutes at approximately 2000 rpm. The suspension sample is then drawn off from the test tube in a third work step and layered on a separating medium (plasmasteril). This is followed in a fourth work step by another centrifuging process lasting approximately ten minutes at 500 rpm. The fractionated column thus obtained is prepared in the fifth work step so that the proximal fraction (supernatant) and the distal fraction (plasma) are separated by pipetting.

In the sixth work step, a slide is inserted in a centrifugal chamber, whereby the proximal fraction (supernatant) is added to one bore and the distal fraction (plasma) is added to the other bore.

This is followed by the seventh step involving a third centrifuging process, approximately ten minutes at 2000 rpm.

During the centrifuging process the heavier epithelial cells migrate in the fluid under the influence of the centrifugal force exerted on them toward the slide, and are deposited in the form of a sediment.

Following sedimentation on the slide of the cells to be investigated, the liquid residue in the centrifugal chamber is drawn off by a pump and the slide, coated with the cells to be investigated, is placed in a 96% alcohol solution. The slide is then Pap stained. The epithelial cells are sedimented onto one field on the slide whose bore was filled with the distal fraction, while another type of cells is sedimented on the adjacent field of the same slide, with which the bore which was filled with the proximal fraction (supernatant) is associated. This sedimented field serves only to demonstrate that insignificant parts of desired epithelial cells are still present in the supernatant, and that the first slide is therefore a representative image of the smear.

One disadvantage of the known method is that a triple centifuging process is required, which takes considerable effort and time. The second centrifuging process, in which four mL for example of the standard solution is layered on six mL of the separating medium, and the test fluid thus produced is separated by centrifuging into a proximal fraction (supernatant) and a distal fraction (plasma), whereby the two fractions must then be separated in a time-consuming manner by pipetting, and must be placed in separate bores of the centrifugal chamber, is particularly troublesome.

The goal of the present invention is to devise a method of the type described hereinabove which is less time-consuming and tedious so that one or more steps can be combined into a single work step.

In accordance with advantageous features of the present invention, the separation of the distal and proximal fractions, placing of the distal and proximal fractions in a bore of the centrifugal chamber, and coating of a slide in the centrifugal chamber with epithelial cells from the distal and proximal fractions on separate areas of the slide are carried out or performed during a single centrifuging process.

Therefore, according to the invention, the separation into a distal and a proximal fraction together with their introduction into separate bores of a centrifugal chamber and the centrifuging of the two fractions with sedimentation on the slide is performed in a single step during the centrifuging process. This saves considerable effort, since previously these steps had to be performed with the centrifuge stopped and with the centrifugal chamber removed. This is avoided according to the invention and the work steps are performed in sequence in a single work step during the centrifuging process.

In accordance with further features of the present invention, it is possible not only to sequentially perform the separation of the distal and proximal fractions, placing the same into the bores of the centrifuge chamber, and coating separate areas of a slide in the centrifuge chamber during a single centrifuging process, but also to stain the cells sedimented on the slide during the centrifuging process as well.

A centrifugal chamber adapted to carry out the method according to the present invention is characterized by the fact that a flow connection such as, for example, a transfer bore or channel, is disposed between the bores which are arranged parallel and at a distance apart. During the centrifuging process, therefore, the fluids are conducted from one bore into the adjacent bore.

As has already been outlined above, the second centrifuging process is introduced so as to achieve a clean background when viewing the area of the slide which is sedimented (layered) with epithelial cells, with the optimum cell density possible. By providing a flow connection between the two test bores, it is ensured that separation into the distal and proximal fractions will occur during centrifuging and that the proximal fraction will be conducted via the flow connection according to the invention into the adjacent bore of the centrifugal chamber during the same centrifuging process. Hence, cleaning the cell samples to remove undesired leukocytes and cell debris as well as centrifuging the cells are accomplished in a first work step.

Providing a flow connection between the two above-mentioned bores can also eliminate the work step in which the suspension sample is centrifuged in a normal test tube and is separated into a proximal and a distal fraction, whereupon the two fractions are separated by pipetting and loaded manually into separate bores in the centrifugal chamber. This is eliminated according to the invention since the plasmasteril solution is immediately loaded according to the invention into one bore of the centrifugal chamber, while the sample suspension is layered on this plasmasteril solution. The centrifugal chamber thus prepared is placed in the centrifuge rotor and, as later described, a centrifuge chamber equipped according to the invention may be used, either with a horizontal head with swinging supports or one with an angle head.

Separation of the layered sample suspension into a proximal and a distal fraction takes place during the centrifuging process, whereby the distal fraction is transferred to the adjacent bore by the arrangement of the flow connection between the two bores during the centrifuging process, so that after this process is over, the epithelial cells are already sedimented on the slide located below after completion of the centrifuging process in one bore of the centrifugal chamber, while the residue is sedimented on the slide in the adjacent bore.

The process described above is therefore considerably simplified by the technical teaching proposed according to the invention.

A plurality of solutions is proposed within the framework of the present invention describing how the distal fraction can be conducted out of one bore into the adjacent bore via the flow connection according to the invention. A first group of solutions proposes that the transfer through the flow connection be accomplished exclusively by centrifugal force, while a second group of solutions proposes that compressed air be introduced into the bore which contains the distal and proximal fractions together, with the air forcing the distal fraction through the above flow connection into the adjacent bore.

The inventive idea of the present invention, however, is not merely limited to providing a flow connection in the form of a channel or a transfer bore between two adjacent bores. According to the invention, not only can two adjacent bores be connected together by flow connections located therebetween, but also more than two, e.g. three, four, or even more bores, can be arranged in series through flow connections disposed therebetween. This produces unexpected advantages, which will be described hereinbelow.

By adding a third bore in series with the second bore, the advantage is achieved that staining or some other treatment of the cell bodies sedimented on the slide is possible. The third bore acts as a waste chamber for the fluid drained off from the first and second bores into the third bore. After the epithelial cells have been sedimented on the slide field disposed beneath the first and second bores, the two bores are emptied. The contents of the first bore are transferred to the second bore by application of compressed air, and fill the second bore. The compressed air acts, through the first bore and via the connecting channel between the first and second bores, on the second bore, forcing the fluid collected therein through another channel into the third adjacent bore. The contents of the first and second bores collect in this bore. After the first and second bores have been completely emptied by applying compressed air, staining fluid is introduced into the first bore. According to a first embodiment, which will be described in greater detail hereinbelow, the centrifuge is stopped at this point and a small quantity of staining fluid is introduced into the first bore. The centrifuge is then restarted and the staining fluid is conducted by centrifugal force against the slide field where it stains the cell bodies stored thereon. Compressed air is then added during the centrifuging process and all of the staining fluid is introduced via the connecting channel between the first and second bores into the second bore. As the centrifuging process continues, the cell bodies resting on the slide field are stained as well. The centrifuge is then stopped and compressed air is introduced into the first bore while the centrifugal chamber is at rest, with the air flowing through the first empty bore and then through the connecting channel into the second bore, and forcing the staining fluid resting on the bottom of the second bore through a channel terminating at this point into the third bore of the centrifugal chamber. This third bore then receives the staining fluid in addition to the liquid previously collected therein. By using the procedure described, it is possible in addition to performing the centrifuging process for sedimentation of cell bodies on various areas of the slide field, also simultaneously to perform a staining process in a simple fashion, without the slide having to be removed from the centrifugal chamber for the purpose and having to be subjected to tedious staining methods.

After the stain from the first and second bores has been bleached, it is possible, in accordance with further features of the invention, to add still other fluids and to expose the slide fields of the first and second bores thereto. This is possible for example by adding a fixing fluid, which fixes the stained cells on the slide field. Likewise, special rinsing fluids may be added, whereby the procedure described previously is performed.

Provision is made according to the invention for various fluids, e.g. staining fluid, fixing fluid, or rinsing fluid to be introduced during the centrifuging process. Therefore it is no longer necessary, as described above, to stop the centrifuge in order to add the staining fluid or the other processing fluid into the first bore with the centrifugal chamber opened, but provision is made according to the further for introducing these fluids into the centrifugal chamber with the centrifuge running and removing these fluids from the two bores likewise with the centrifuge running, in order to convey them into a waste bore. Adding two different processing fluids is accomplished by the two bores being emptied first in the manner described above during a first application of compressed air.

Compressed air is then applied to a reservoir mounted on the centrifugal chamber to cause staining fluid to drip into the first bore from this reservoir.

The staining process then occurs in the manner described above whereby the centrifuge must be stopped at the completion of the staining process in order to convey the staining fluid from the second bore into the third (waste) bore.

By providing additional reservoirs which contain other processing fluids and which are in liquid communication with the first bore of the centrifugal chamber, it is possible to introduce as many processing fluids as desired into the first and second bores during the centrifuging process and finally to remove them again.

The various expulsion possibilities are listed in summarized form below, making it possible according to the invention to transfer processing fluid from the first bore into a second bore and also to drain the second bore and convey the processing fluid located therein into a third and thence into other bores.

According to additional advantageous features of the present invention, preferably, when the flow connection consists of a transfer bore with an adjustable cross section, one bore is divided into a bore with a larger diameter and a bore with a smaller diameter flush therewith, and a transfer bore runs from the neck of the larger into the smaller bore. The chamber with the staggered bore is the loading chamber for the sample suspension and the chamber with the through bore is the transfer chamber. The height of the staggered bore roughly forms the separating layer between the two fractions of different weights. A clamping screw serves to regulate the transfer opening, i.e. to change the cross section of the transfer bore. When centrifuging begins, i.e. when the carriers swing out, overflow into the direction opposite to the centrifugal force has already begun. A tiny slot in the clamping screw permits sufficient supernatant (proximal fraction) to flow into the second bore, with the force being generated by centrifugal force.

Another embodiment of the present invention provides for an overflow chamber with a sealing piece, with the sealing piece having a notch on the bottom thereof.

The dimensions of this notch define the throughflow cross section from one bore into the other. The notch is forced by centrifugal force into the throughflow cross section. Sealing pieces with notches of different depths can be used in order to have a specific cross section from one bore into the other for each case of suspension solution.

An important aspect of the provision of the clamping screw and the sealing piece is that the sample chambers are designed for swinging suspensions, i.e. they are vertical in the resting position and horizontal in the operating position. The plane of the slide to be layered is horizontal in the resting state and vertical in the operating state.

Moreover, the invention provides for the overflow to take place through the flow connection from one bore into the other by compressed air. Sample chambers provided for the purpose are preferably used for a centrifuge with an angle head, wherein the centrifugal chamber does not shift through 90° during the centrifuging process. The sample chambers are placed in the angle head, whereby the recesses for the air connection come to rest on the sealing pieces for the air outlet. The centrifugal chambers are then filled through a vertical filling stub and then, as in the other described embodiments, coated first with six mL of plasmasteril and then with four mL of cell suspension. A cover with a common elastic plate, e.g. a rubber plate, closes all the chambers producing a closed system. The two fractions are rearranged by gravity as the centrifuge runs.

The interface, which was horizontal at rest, orients itself vertically during the centrifuging process. The slide remains in the vertical position. At low centrifugal forces (approximately 60 G) the epithelial cells penetrate the plasmasteril. The supernatant, which otherwise would require a rather long time according to the first embodiment (transfer bore, sealing piece) to flow into the other bore, is driven by compressed air through the centrifuge shaft via the hollow bottom of the angle head and the connecting pieces into the filling stub, so that overflow through the transfer bore is accelerated.

There are two different solutions for employing the above-described sample chambers charged with compressed air. One solution comprises a sample chamber with a staggered bore whereby this bore receives the plasmasteril and the sample suspension. The transfer bore terminates in the smaller bore at the neck of the transition of the larger bore. The second solution relates to a sample chamber with a through bore, into which the plasmasteril and the sample suspension are loaded. A connecting channel is proposed, provided parallel to and a short distance from this bore in the material of the sample chamber, whereby this connecting channel initially has no connection whatever to this bore, and terminates with its end at the slide.

The special feature of this separate connecting channel is that a needle can be used to punch a connecting hole at any distance from the slide, in the wall between the bore which receives the sample suspension and the connecting channel, so that the residual fluid in the bore which receives the sample suspension is variable.

A sample chamber of this kind can consist, for example, of an injection-molded plastic material so that it is readily possible to perforate the wall of the bore receiving the sample fluid with a needle, in order to produce a link to the connecting channel.

Therefore, according to the invention three different possibilities for controlling the flow of fluid from one bore to the adjacent bore are provided. They are either a clamping screw or a sealing piece which change the throughflow cross section of the connecting channel or the introduction of compressed air, which increases the flow velocity in the channel, whereby the clamping screw or sealing piece can be eliminated.

Instead of the means listed above, provision is made in accordance with further features of the invention for disposing a solenoid valve in the connecting channel, said valve being actuated externally to open and close during the centrifuging process.

The invention will now be described in greater detail with reference to drawings showing a plurality of embodiments. Additional features and advantages of the invention essential thereto will be apparent from the drawings and their descriptions.

Figure 4:
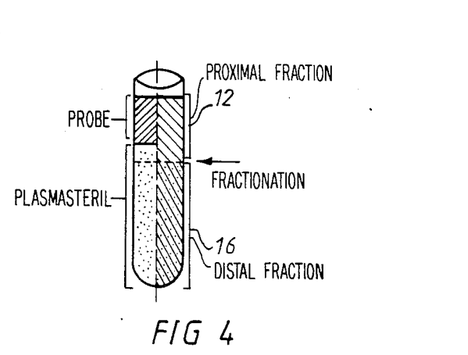
FIG. 4 is a schematic view of the design and fractionation of the separating column in a centrifuge tube before (left) and after (right) sedimentation of the sample.

Referring now to the drawings wherein like reference numerals are used throughout the various views to designate like parts and, more particularly, to FIG. 4, according to this figure, the preparation of proximal fraction 12 and distal fraction 16 is schematically illustrated using an article of laboratory glassware. The sample suspension (in FIG. 4) is layered on a separating medium (plasmasteril). It is then subjected to the centrifuging process and the heavier epithelial cells in the sample suspension migrate through the separating medium toward the distal end of the test tube. Following centrifuging, there is a proximal fraction 12 (supernatant) and a distal fraction 16 (plasma). The epithelial cells to be investigated are preferably found in the distal fraction in a highly concentrated form.

Previously, proximal fraction 12 was separated from distal fraction 16 by pipetting at the level of the arrow marked "fractionation" in order then to centrifuge the distal fraction once more to compel the epithelial cells suspended therein to migrate toward the distal end of the sample chamber (bore) under the influence of centrifugal force and deposit themselves on a slide located there. A description will now be provided with reference to FIGS. 1-3 of how proximal fraction 12 is separated from distal fraction 16 during the centrifuging process (i.e. without pipetting as usual). The pipetting described at the outset for separating the two fractions is avoided.

Figure 1:
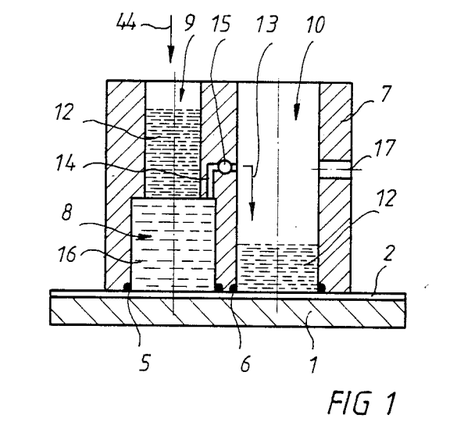
FIG. 1 is a cross-sectional veiw of a centrifugal chamber taken along the line I—I in FIG. 2, whereby the fluid distribution is shown during the centrifuging process.
Figure 2:
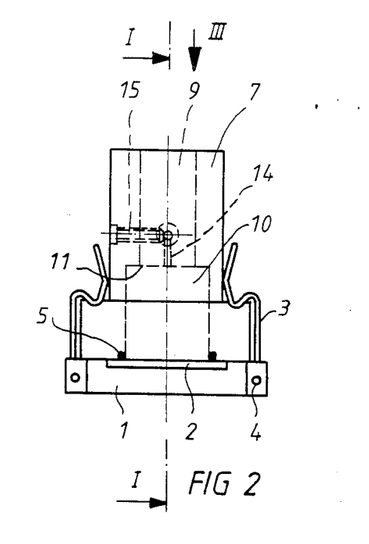
FIG. 2 is an end view of the centrifugal chamber taken in the direction of arrow II in FIG. 3.
Figure 3:
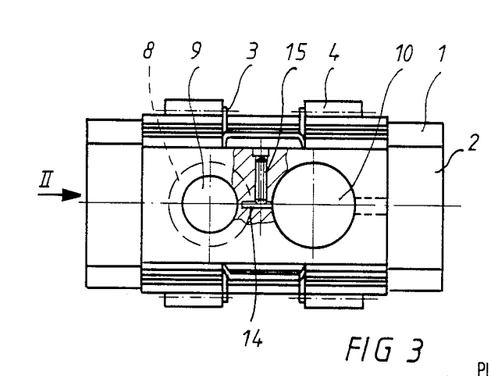
FIG. 3 is a top view of the centrifugal chamber in the direction of arrow III in FIG. 2.

The centrifugal chamber shown in FIGS. 1-3 consists of a sample chamber 7, preferably made of an injection-molded plastic part. Sample chamber 7 is mounted on a slide 2 and sealed off by sealing rings 5 and 6, whereby it is firmly clamped by slide 3 disposed in holders 4 on the side of a carrier plate 1, against this carrier plate 1, on which slide 2 is disposed. The left bore in sample chamber 7 consists of an upper, smaller bore 9 and a lower, larger bore 8 flush therewith, whereby a neck is provided between the two bores 8 and 9.

In addition to staggered bore 8, 9 another bore 10 is disposed parallel and at a distance, with a through bore 17 provided in the bore wall at a distance above the plane of slide 2, said through bore 17 being flush with horizontal transfer bore 14 and serving to produce the latter.

Transfer bore 14 is disposed in such a way that it runs from the transition of small bore 9 to larger bore 8 and terminates in the bore 10. Clamping screw 15 is inserted in a threaded bore in sample chamber 7, with the screw 15 having its tip projecting into the cross section of transfer bore 14. By turning clamping screw 15 in or out to a greater or lesser degree, the cross section of transfer bore 14 can be adjusted.

Before the centrifuging process begins, the separating medium (e.g. plasmasteril) (see FIG. 4) is loaded into left bore 8, 9, with the separating medium being coated by the sample suspension.

According to the later description in conjunction with FIGS. 10-12, it will be explained that the complete sample chamber 7 is placed in a cradle suspension with a centrifuge, so that the plane of slide 2 is vertical during the centrifuging process and the longitudinal axes of bores 8, 9 and 10 are aligned horizontally. Sample chamber 7 is then inserted in an angle head rotated at 90° relative to the illustration in FIG. 1, so that the left-hand vertical wall of bore 9 is parallel to the bottom and the right-hand vertical wall of bore 10 is parallel to the cover of the angle head. The centrifugal force then acts as shown in FIG. 1 in the direction of the longitudinal axis of bores 9 and 10 downward in the direction of slide 2 located at the distal end (direction of arrow 44).

FIG. 1 is a schematic representation of the separation of the sample into a proximal fraction 12 and a distal fraction 16, during the centrifuging process, whereby the epithelial cells of the sample suspension diffuse into the separating medium and are sedimented by centrifugal force on the lower end of bore 8 on slide 2.

To separate proximal fraction 12 (supernatant) from the distal fraction during centrifuging, the proximal fraction 12 is gradually forced by the centrifugal force directed downward in the longitudinal direction of bore 9, into bore 8, creating an overpressure which is relieved by transfer bore 14, which terminates at neck 11 of bore 8.

Proximal fraction 12 will therefore flow slowly in the direction of arrow 13 through transfer bore 14 and flow into the bore 10. Depending on the duration of the centrifuging process and the setting of clamping screw 15, more or less time will be required until the total proximal fraction 12 has flowed into the bore 10.

Thus, sedimentation of proximal fraction 12 on the observation field of slide 2 takes place during the continuation of the centrifuging process at the end of the bore 10.

Therefore, the proximal and distal fractions are sedimented on a slide 2 in a single centrifuging process, whereby the tedious separation of the two fractions by pipetting and subsequent preparation is eliminated.

Figure 8:
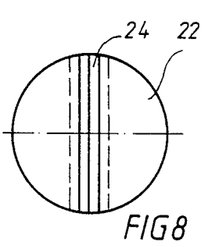
FIG. 8 is a bottom view of the sealing piece.
Figure 9:
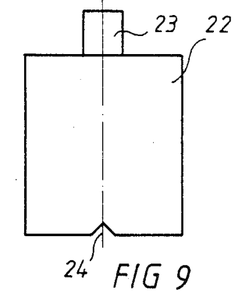
FIG. 9 is a side view of the sealing piece according to FIG. 8.

In the sample chamber of the embodiment of FIGS. 5–9, the only difference is that instead of a clamping screw a sealing piece 22 is used which is shown in greater detail in FIGS. 8, 9. The bottom of sealing piece 22 comprises a radial through connecting channel 24 in the form of a notch with a conical cross section. The sealing piece is displaceable axially in an associated bore in sample chamber 30, whereby connecting channel 24 of sealing piece 22 constitutes the connection between a left transfer bore 19, which terminates in the larger bore 8, and a right transfer bore 20, which terminates in the bore 10.

The greater the centrifugal force, the greater the force with which sealing piece 22 with its connecting channel 24 is pressed against the flat surface between connecting bores 19 and 20, and the smaller the throughflow cross section. Sealing piece 22 can be made from an elastic plastic, which deforms under the influence of centrifugal force, producing a reduction of the cross section. Sealing piece 22 can be removed from sample chamber 30 by means of a handle 23.

Figure 5:
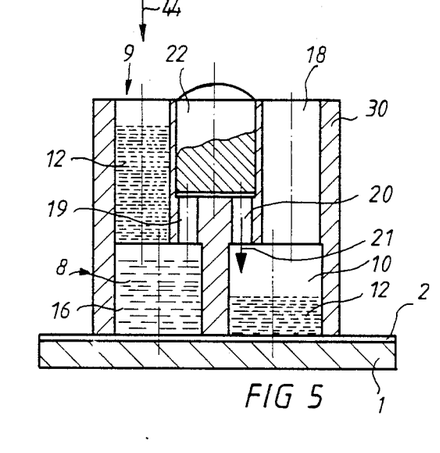
FIG. 5 is a cross-sectional view taken along the line V—V in FIG. 6 through a second embodiment of a centrifugal chamber, whereby the fluid distribution is shown during the centrifuging process.
Figure 6:
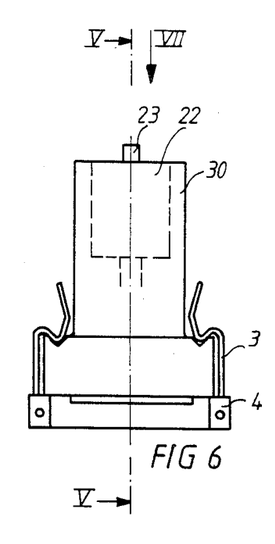
FIG. 6 is an end view of the centrifugal chamber in the direction of arrow VI in FIG. 7.
Figure 7:
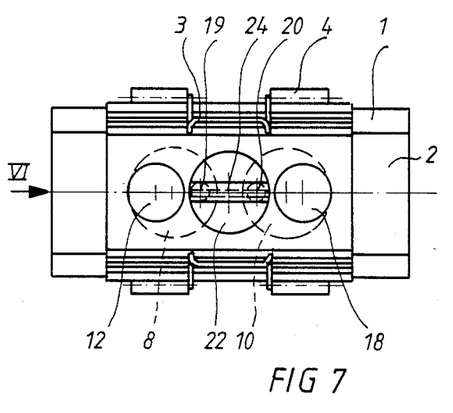
FIG. 7 is a top view of the centrifugal chamber of the second embodiment taken in the direction of arrow VII in FIG. 6.

During the centrifuging process, likewise under the influence of the centrifugal force acting in the direction of arrow 44, the sample suspension loaded in left bore 8, 9 is separated into a distal fraction 19 and a proximal fraction 12, stratified above it. Since transfer bore 19 again departs from neck 11 between bores 8 and 9, the pressure acting on proximal fraction 12 because of the prevailing centrifugal force is drained away via a transfer bore 19, connecting channel 24 and transfer bore 20, so that proximal fraction 12 flows in the direction of arrow 21 into right bore 10 and is sedimented there on the slide 2.

Right bore 10 has a staggered smaller bore 18 offset above it.

Figure 10:
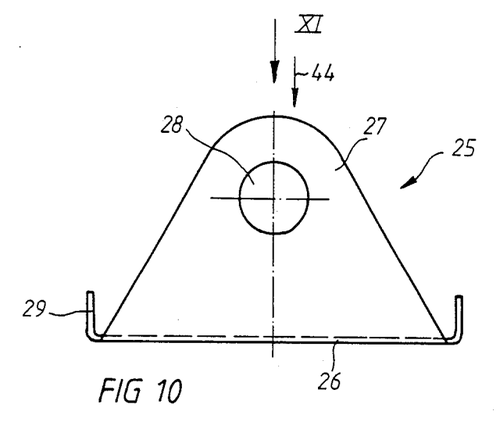
FIG. 10 is a side view of a cradle (cradle suspension) for use with the centrifugal chambers shown in FIGS. 1-3 and 5-7 in a side view.
Figure 11:
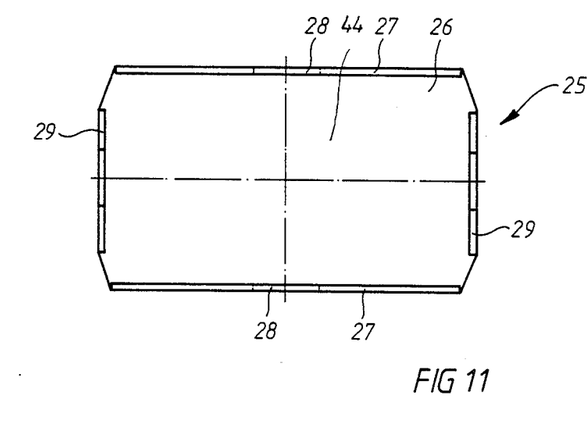
FIG. 11 is a top view of the cradle looking in the direction of arrow XI in FIG. 10.
Figure 12:
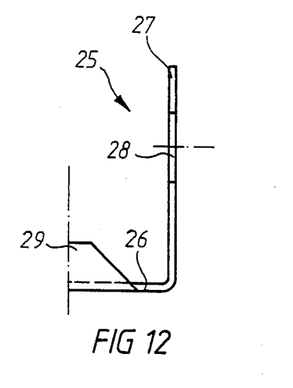
FIG. 12 is a partial side view of the cradle.

FIGS. 10–12 illustrate a cradle suspension generally designated by the reference numeral 25, as used with sample chambers 7 and 30 shown in FIGS. 1–3 and 5–7. The cradle suspension 25 shown therein includes a carrier plate 26, having a lateral and opposite edge 29. Legs 27 are mounted on the edge of carrier plate 26, rotated through 90° with respect thereto, with the legs each being traversed by a bore 28. The bores 28, located opposite one another, are traversed in a manner not shown in detail by a carrier pin fastened to the centrifuge rotor. Sample chamber 7, 30 together with its carrier plate 1 is placed on carrier plate 26 of cradle suspension 25, whereby the raised edge 29 and the laterally projecting legs 27 prevent sample chamber 7, 30 from falling off cradle suspension 25. During the centrifuging process, cradle suspension 25 with its bore 28 swings around the carrier pin so that carrier plate 26 is vertical, as are carrier plate 1 and slide 2 on sample chamber 7, 30 located parallel thereto.

Figure 18:
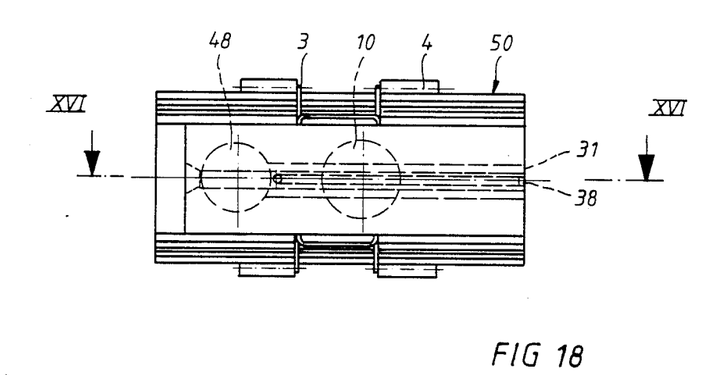
FIG. 18 is a top view of the centrifugal chamber looking in the direction of arrow XVIII in FIG. 16.
Figure 19:
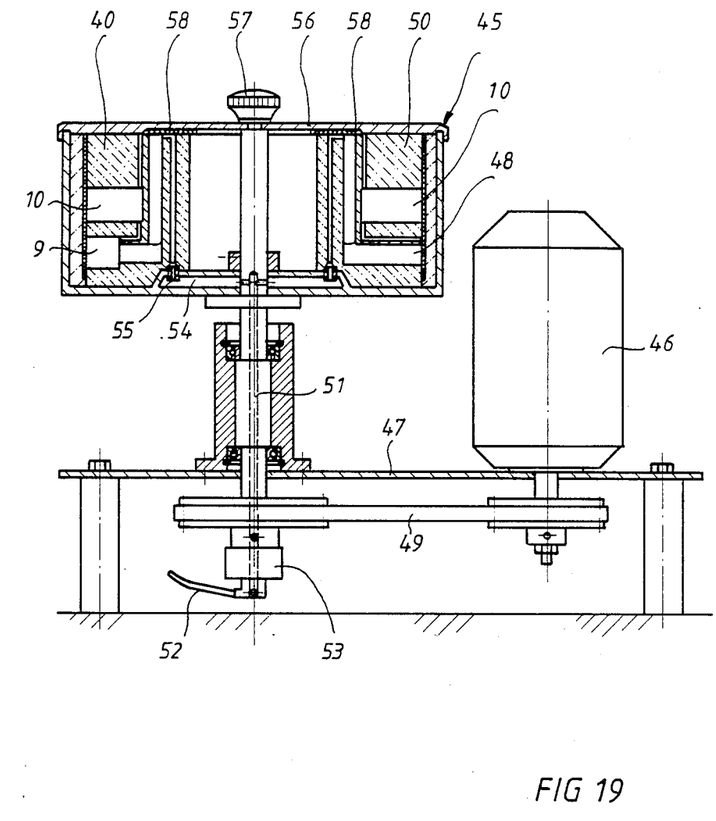
FIG. 19 is a partially schematic cross-sectional view of an angle head 4 use with two different centrifugal chambers.
Figure 20:
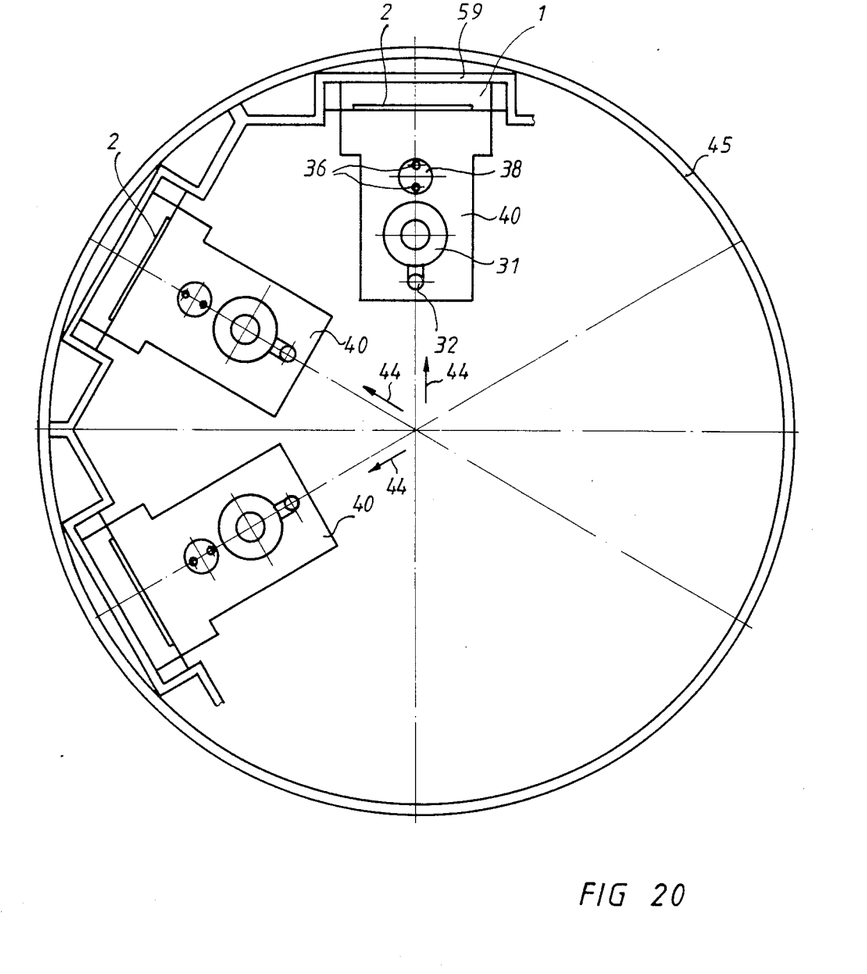
FIG. 20 is a top view of the angle head according to FIG. 19 showing the use of a centrifugal chamber according to the embodiment shown in FIGS. 13-15.

Sample chambers 40 and 50 illustrated in FIGS. 13–15 and 16–18 are an angle head 45 shown in FIGS. 19 and 20. The installed position of the sample chambers 40, 50 is shown in FIG. 19. The important feature here is that a cradle suspension is eliminated, and that the sample chambers 40, 50 are inserted so as to rest directly in angle head 45. Therefore, the position of sample chambers 40, 50 does not change either in the resting position or in the working position, i.e. carrier plate 1 with slide 2 located behind it is always perpendicular and the left-hand vertical wall of bore 9, shown in FIGS. 13–15 and 16–18, forms the bottom of sample chamber 40, 50. Sample chamber 40 shown in FIGS. 13–15 also has a carrier plate 1 with a slide 2 mounted thereon, whereby sample chamber 40 is pressed against the slide and against carrier plate 1 by the holder 4 described previously and clips 3.

Bore 8, 9, which receives the sample suspension and the plasmasteril solution, is filled through a filling stub 31 which is shown in FIG. 20 in the installed position, vertical, with its mouth upward.

Figure 13:
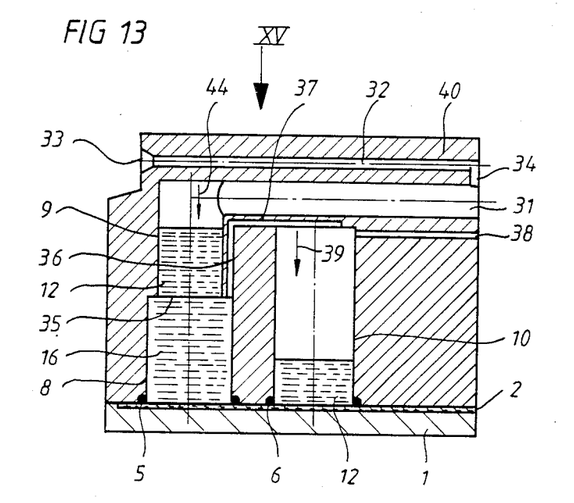
FIG. 13 is a cross-sectional view of a third embodiment of a centrifugal chamber taken along the line XIII-—XIII in FIG. 15, whereby the fluid distribution is shown during the centrifuging process.

During the centrifuging process, again under the influence of the centrifugal force acting in the direction of arrow 44, as shown in FIG. 13, a proximal fraction 12 and a distal fraction 16 are formed in the bores 8, 9 in the left chamber which are located one above the other and flush with one another. Compressed air is used to separate proximal fraction 12 from distal fraction 16 during the centrifuging process. The compressed air is supplied, as shown in FIG. 19, through a compressed-air hose 52 and a compressed-air connection 53 to rotor shaft 51 of the centrifuge, whereby it passes through a distributor channel 54 disposed in the bottom of angle head 45 into connecting pieces 55, which engage a suitable conical receiving bore (connecting piece 33) in FIGS. 13 to 16. Proceeding from connecting piece 33 (FIGS. 13–16) the compressed air is conducted by a pressure channel 32 to the top of sample chamber 40, 50. The transfer to the mouth of filling stub 31 is accomplished by providing a connecting piece 34, open on one side, between the mouth of compressed-air channel 32 and the mouth of filling stub 31, and covering these parts in an airtight fashion with an elastic plate 58, disposed on the underside of cover 56 of angle head 45. This produces an airtight connection between compressed-air hose 52 and filling stub 31. The compressed air then acts in the direction of arrow 44 on the surface of proximal fraction 12, which is conducted, because of the pressure differential, by a connecting channel 36 and a piece 37 in the direction of arrow 39 into the bore 10. Bore 38 terminates next to elastic plate 58 as shown in FIG. 19 and serves for venting.

Figures 16, 17:
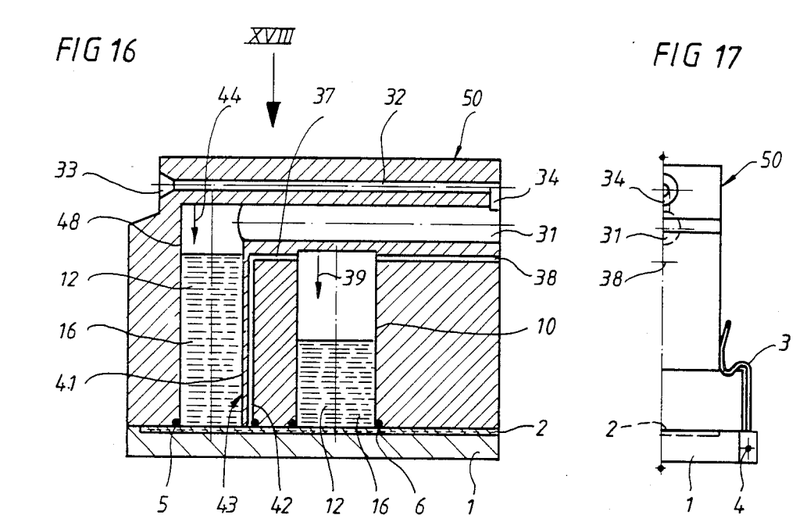
FIG. 16 is a cross-sectional view taken along the line XVI—XVI in FIG. 18 through a fourth embodiment of a centrifugal chamber; the fluid distribution is shown during the centrifuging process.
FIG. 17 is an end view of the centrifugal chamber according to FIG. 16.

The embodiment of a sample chamber 50 according to FIGS. 16–18 proposes a pneumatically charged transfer chamber with transfer channel (connecting channel 42) and vent (bore 38) leading to slide 2.

Figure 14:
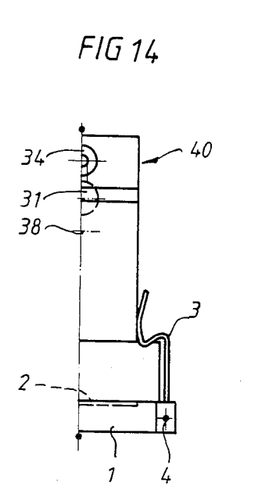
FIG. 14 is an end view of the centrifugal chamber according to FIG. 13.
Figure 15:
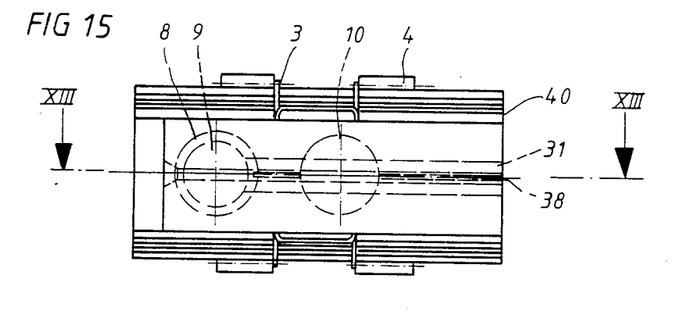
FIG. 15 is a top view of the centrifugal chamber taken in the direction of the arrow XV in FIG. 13.

In the embodiment of FIGS. 13–15, instead of a staggered bore 8, 9 as shown in the embodiment in FIGS. 13–15, a through bore 48 is provided, and that connecting channel 42 runs parallel to and at a distance from this bore 48 in the material composing sample chamber 50 runs parallel and at a distance from this bore 48. It is now possible to perforate wall 41 or 48 of bore 48 with a needle; the perforation can take place, for example, at the level of arrow 43, so that the connection to connecting channel 42 from bore 48 can be made at any previously determined height (distance from slide 2). It is then possible to vary the amount of fluid remaining in bore 48.

Connecting channel 42 which runs vertically in FIG. 16 merges with a horizontal section 37 and terminates in right bore 10. A bore 38 which serves to vent bore 10 terminates next to an elastic plate 58 as shown in FIG. 19.

The free choice of fractionation boundary made possible by perforating connecting channel 42 in the direction of the arrow 43 makes it possible to obtain a distal and a proximal fraction 12, 16 both in left bore 48 and in right bore 10, whereby the two bores contain fractions of different weights.

As shown in FIG. 20, the sample chamber 40 or 50 is inserted in the position shown in FIG. 19 in a vertical rotor frame 59 and then locked in position. Cover 56, with elastic plate 58 beneath it, can then be put in position so that compressed-air hose 52 is connected in an airtight fashion with filling stub 31 of sample chamber 40 or 50. Cover 56 is tightened in place with the knob 57. Cover 56 with elastic plate 58 simultaneously serves as a tensioning means for the sample chamber 40 or 50. The centrifuge is then turned on, with motor 46 mounted on a support plate 47 and driving rotor shaft 41 through a drive belt 49.

Figures 21, 22:
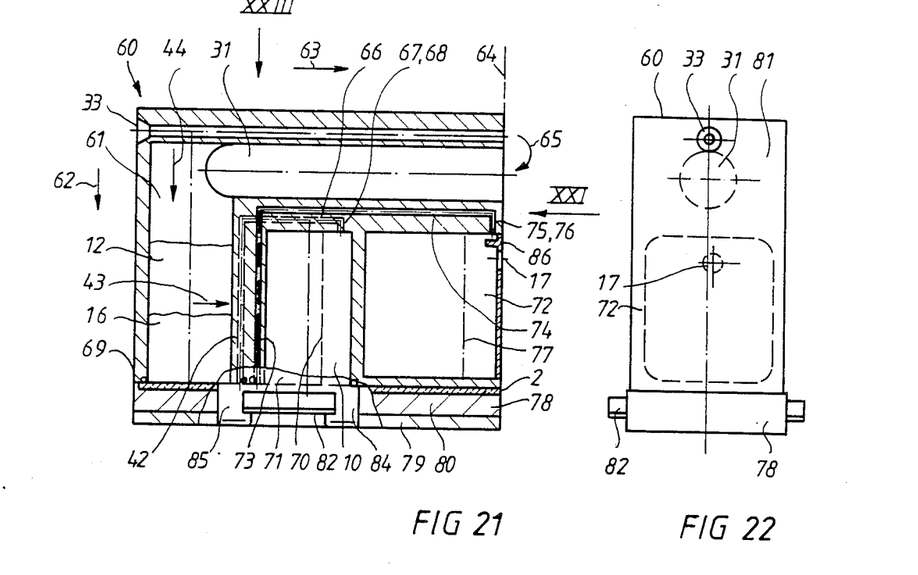
FIG. 21 is a cross-sectional view of a fourth embodiment of a centrifugal chamber taken along the line XXI-—XXI in FIG. 23.
FIG. 22 is an end view of the centrifugal chamber shown in FIG. 21.
Figure 23:
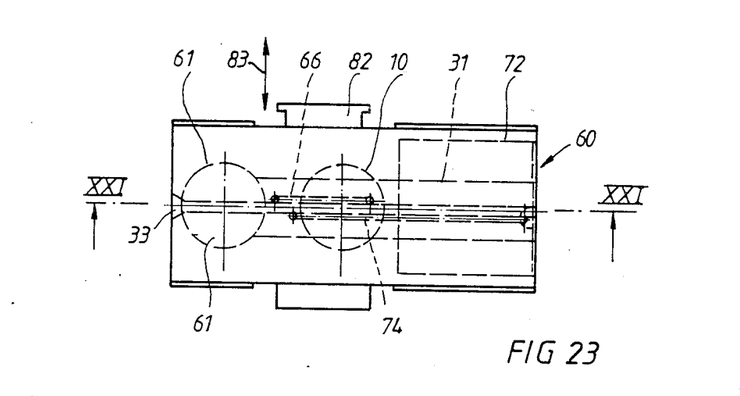
FIG. 23 is a top view of the centrifugal chamber shown in FIG. 21 looking in the direction of arrow 23 in FIG. 21.
Figure 24:
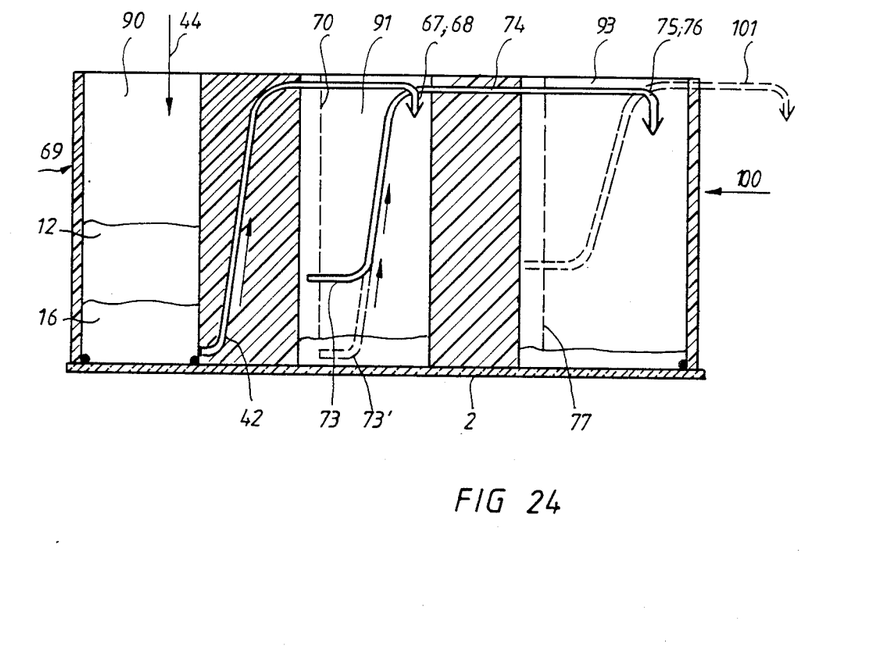
FIG. 24 is a schematic longitudinal cross-section view of a fifth embodiment of a centrifugal chamber.

As shown in FIGS. 21-23, a large bore 61 is provided, in which proximal fraction 12 and distal fraction 16 are deposited during the centrifuging process in the manner described above. After separation is complete, compressed air is introduced into channel 33 during the centrifuging process, with the air flowing into the channel in the direction of arrow 63 and is then deflected by cover 56, shown in FIG. 19, in the direction of arrow 65, flowing into bore 61 via channel 31 in the direction of arrow 44. Here the sample fluid is forced through channel 42 and flows into second bore 10. The expansion of this embodiment with respect to the embodiment shown in FIG. 16 resides in the fact horizontal section 37 in FIG. 16 is omitted, and that a section 66 is provided instead, with the section 66 merging with another section 67 of the channel. The important feature here is that mouth 68 of section 67 comes to rest in small bore 10 when the sample chamber is upright, i.e. when the sample chamber is resting on bottom 69, above the level of the fluid that forms when the sample chamber is in the standing position, so that flow of sample fluid 71 from second bore 10 via sections 66 and 67 and channel 42 back into first bore 61 is reliably prevented.

It is also possible according to the invention to provide a third bore 72 connected in series with second bore 10. The important thing is that a channel 73 terminates below the level of fluid 70 in second bore 10 when the sample vessel is standing. The opening in the embodiment shown in FIG. 21 is located directly above slide 2, leaving a slight amount of play amounting to 2/10 of a millimeter; however, this opening can be provided anywhere in the area (e.g. at the point indicated by arrow 43) in centrifuge channel 73. Channel 73 continues as a vertical channel 74, which becomes a further horizontal channel 75, which terminates in bore 72. The important thing is that mouth 76 of channel 75 is located above the level of fluid 77, so that no fluid can flow back into the second sample chamber from the third bore 72 either, when the centrifuge is at rest.

The provision of a third bore 72 behind second bore 10 and its connection via channels 73, 74, and 75 represents a considerable advance in cytology, because such a sample vessel, especially one with three bores, permits staining to be performed during the centrifuging process. This is accomplished as follows:

Starting with proximal fraction 12 and distal fraction 16, which are formed in first bore 61, compressed air is then supplied via channel 33, which forces all of the fluid in bore 61 in the direction of arrow 44 through channel 42, 66, 67, 68 into second bore 10. The centrifuge is then stopped and the fluid assumes a position with a level 70. Compressed air is then added via channel 33, which then flows through empty sample chamber 61, thence via channel 42, 66, 67, 68 into second bore 10, pressurizing the sample fluid and forcing it into the third bore 72 via channel 73, 74, 75.

The provision of a third bore 72 is important because it permits staining to be performed after the first two sample chambers have been freed. The centrifuge is stopped, the cover opened, and a few drops of staining fluid added via filling stub 31 into first bore 61. After the sample fluid has been added, the centrifuge is turned on and the sample fluid is forced against the slide surface of first bore 61, staining the epithelial cells located therein. A certain space of time is allowed to elapse for the stain to act, whereupon compressed air is added via channel 33, which acts in the direction of arrow 44 on the staining fluid located in the vicinity of the slide surface, said fluid then being forced into second bore 10 via channel 42, 66, 67, staining the slide field located there. After a suitable period of time for allowing the stain to act has been permitted to elapse, the centrifuge is stopped and the staining fluid flows downward to the bottom, parallel to fluid level 70. Channel 73 from bore 72 terminates in the vicinity of this bottom in bore 10, so that while sample chamber 60 is at rest and while the compressed air is being added, the air flows in the direction of arrow 44 into first bore 61, then via channel 42, 66, 67 into second bore 10, forcing the staining fluid then via the opening of channel 73 at the slide surface into channel 73, and via channel 74, 75 and opening 76 into third bore 72. A waste fluid is collected in third bore 72, consisting of a mixture of sample fluid and staining fluid. To prevent the fluid from flowing out of through bore 17, which serves for venting, a projection 86 is provided between opening 76 of channel 75 and through bore 17.

After the staining process is complete, additional fluid can be added in a similar fashion, i.e. a rinsing fluid, a fixing fluid, or the like, whereupon all the used solutions then accumulate in bore 72 after all of the work steps have been executed.

Connecting several bores 61, 10, 72 in series and suitably connecting these bores 61, 10, 72 with the aid of channels allows the slide surfaces of slide 2 of bores 61, 10 (i.e. the test surface and the control surface of the slide) to be processed with different processing fluids, without ever having to remove the entire sample chamber 60 from the centrifuge rotor.

FIGS. 21-23 show a holder which makes it possible to remove the entire bottom plate 78, composed of two partial plates 79 and 80, simply from top part 81. It is possible by shifting sample chamber 60 of a sliding element 82, with a single handle, to release bottom plate 78 from upper part 81, so that slide 2 can be removed directly. The sliding element is displaceable in the direction of arrow 83 and cooperates with corresponding retaining noses 84, 85 on the upper part.

FIG. 23 is a schematic representation of the basic principle intended to make the idea of the invention clearer, showing how the three bores in FIG. 21 are connected in series. The liquid flows are also shown and the openings of the channels can be seen. The dashed lines in second bore 91 indicate that a second channel 73 can be provided. Channel 7, shown by solid lines in second bore 91, is intended to ensure that the sample fluid can only be removed from second bore 91 when the centrifuge is held still, so that the fluid flows onto the bottom and forms fluid level 70 there, so that it can be conducted via channel 73 out of second bore 91 into third bore 93. However, if the transfer from the second to the third bore is to be performed during the centrifuging process, a flow connection corresponding to channel 73' indicated by the dashed lines is chosen, terminating in the vicinity of slide 2. Although the fluid that flows into second bore 91 is directly forced into third bore 93 via channel 73' under the influence of the compressed air, the cross section of channel 73' can be made sufficiently small that the time required for the sample fluid to act on slide 2 in second bore 91 is maintained.

In other words, the cross section is selected so that, for example, after only about two minutes the contents of second bore 91 are completely transferred to third bore 93, ensuring an acting time of two minutes in second bore 91.

Figure 25:
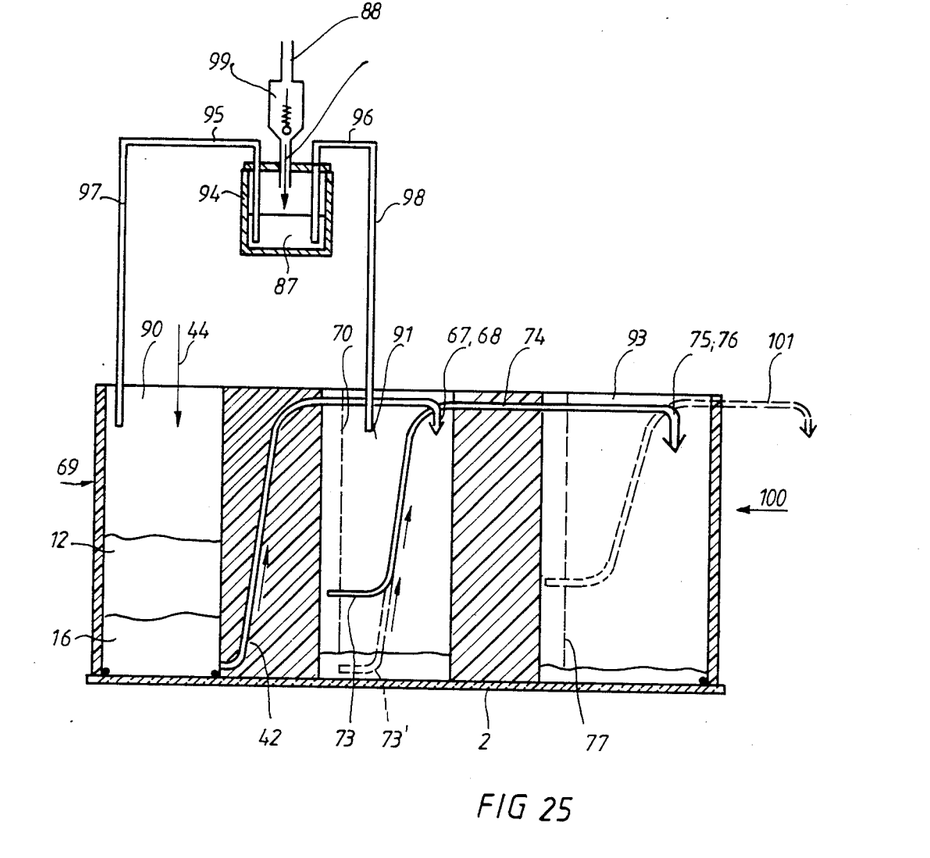
FIG. 25 is a partially schematic longitudinal cross-section view of a sixth embodiment of a centrifugal chamber.

FIG. 25 shows another modified embodiment, in which it is indicated that by using another reservoir (stain reservoir 94 for staining fluid), a staining process can be executed immediately without stopping the centrifuge and opening the centrifuge cover, by emptying the two sample chambers 61 and 10 beforehand, as shown in FIGS. 21-23. If compressed air is then added to a stain reservoir 94 via a second compressed-air line 88, which is disposed approximately parallel to channel 33 in the sample chamber, stain 87 will then be forced via transfer 95, 96 out of stain reservoir 94 and will pass immediately into bores 90, 91 via lines 97, 98. This avoids the need to stop the centrifuge and add stain 87 first to first bore 61 and then transfer it to second bore 91. Instead, stain 87 is distributed in parallel to both bores 91, 92 with the centrifuge running thereby shortening the processing time.

As soon as staining is complete, staining fluid can be removed in the manner described hereinabove from bores 90, 91 whereby the compressed air is added in the direction of arrow 44 to first bore 90, so that stain 87 is transferred via first bore 90 via channel 42 to second bore 91. When first bore 42 is emptied, second bore 91 is likewise emptied via channel 73, 74, 75 and all the stain 87 flows into third bore 93. Additional bores, not shown, can be provided in series downstream from third bore 93. For example, a flow connection from third bore 93 into another bore, not shown in greater detail, is shown in the form of an additional channel 101. Since compressed air is forced back into stain reservoir 94 via lines 97, 98 during introduction of compressed air in the direction of arrow 44 in inadmissible fashion, escaping via compressed-air connection 88, a check valve 99 is provided at this point.

Similarly, the sample shown in FIG. 25 can have any number of processing fluid reservoirs, e.g. a second reservoir for rinsing fluid or a third reservoir for a fixing fluid, and so on.

The important feature of the embodiment of FIG. 25 is that a separate compressed-air connection with a corresponding check valve must be provided for each reservoir 94, to ensure the outward flow from the corresponding reservoir at the proper point in time.

The proposed system therefore has the advantage that sample chamber 100 always stays in the centrifuge and the staining process takes place under centrifugal force in the centrifuge itself and costly, delicate, and inaccurate automatic staining devices are avoided. In particular, assurance is provided that epithelial cells will not be washed off the slide surface during the external staining process, something which is a great disadvantage of previously known staining methods.

However, not only the staining process according to the present invention can be automated, but also the fixing process, the rinsing process, and the like.

It is also important for the complete sample chamber 7, 80, 40, 60, 100 to be made of a relatively inexpensive plastic injection-molded material, simple to manufacture, and that even the O-rings can be replaced by lip seals injection-molded in place, so that it is possible to manufacture such a sample chamber as a disposable article with a low purchase price.

While I have shown and described several embodiments in accordance with the present invention, it is understood that the same is not limited thereto but is susceptible to numerous changes and modifications as known to one having ordinary skill in the art and we therefore do not wish to be limited to the details shown and described herein, but intend to cover all such modifications as are encompassed by the scope of the appended claims.

I claim:

1. A centrifuge chamber for cytodiagnostic investigation of epithelial cells contained in a test sample comprising a carrier plate, a slide fastened on said carrier plate, a sample chamber resting on said slide, said sample chamber including means defining a plurality of bores, said bores being spaced from each other and arranged parallel to each other and being fillable with a sample fluid, each of said bores terminating in end openings, means sealing said bores, at said end openings thereof, to said slide whereby said end openings rest in a sealed fashion on the slide, a flow connection means connecting the bores with each other so as to enable a production of two different slide fields on a single slide from a single sample introduced into the sample chamber.

2. The centrifuge chamber according to claim 1, wherein said bores are arranged such that at least one fluid is conducted into the plurality of bores when the chamber is centrifuged.

3. The centrifuge chamber according to claim 1, wherein the flow connection means comprises a means for defining at least one transfer bore, which transfer bore connects adjacent ones of said plurality of bores, means for varying a cross section of said at least one transfer bore, one of said connected plurality of bores of said connected pair thereof comprises a first bore portion of a large diameter and a second coaxial bore portion of a smaller diameter, and wherein each transfer bore is connected adjacent the smaller diameter bore portion at a shoulder provided on the first bore portion.

4. The centrifugal chamber according to claim 3, wherein said means for varying the cross-section of said at least one transfer bore includes a clamping screw having a tip projecting into the transfer bore for adjusting the cross-section of the transfer bore.

5. The centrifuge chamber according to claim 3, wherein at least two transfer bores are provided, said means for varying the cross section of the transfer bore comprises a clamping element, displaceable axially in a longitudinal direction of the plurality bores, and wherein one end of said clamping element includes a radially extending connecting channel means for forming a connection passage between the two transfer bores.

6. The centrifuge chamber according to claim 1, wherein at least one channel means is provided for conducting fluid from a first of said plurality of bores into at least one adjacent non-coaxial bore, the channel means connecting the adjacent bores connects a lower portion of the first bore and an upper portion of an adjacent bore opposite the slide, and whereby, when the chamber is centrifuged, fluid in the first bore is driven by compressed air through the channel means into the adjacent bore.

7. The centrifuge chamber according to claim 6, wherein said channel means further includes means for conducting at least one fluid into the first bore, and successively through the channel means into additional bores connected in series downstream of the first bore.

8. The centrifuge chamber according to claim 7, wherein said conducting means conducts a plurality of fluids into the first bore.

9. The centrifuge chamber according to claim 8, wherein said conducting means conducts at least one of a staining and fixing fluid.

* * * * *